United States Patent
Rinehart et al.

Patent Number: 6,028,077
Date of Patent: Feb. 22, 2000

[54] CRAMBESCIDIN COMPOUNDS

[76] Inventors: Kenneth L. Rinehart, 1306 S. Carle Ave., Urbana, Ill. 61801; Jiang-Gong Shi, c/o Mei-Fang Liu Qi Li He Agency of Chinese Agricultural Bank, Qi Li He, Lanzhou Gansu Province, China; Furong Sun, 2310 Blackthorn, Champaign, Ill. 61821

[21] Appl. No.: 09/058,507

[22] Filed: Apr. 10, 1998

Related U.S. Application Data

[60] Provisional application No. 60/043,327, Apr. 15, 1997.
[51] Int. Cl.⁷ .................. A61K 31/505; C07D 498/27
[52] U.S. Cl. ................. 514/267; 514/257; 544/231
[58] Field of Search ........................... 514/257, 267; 544/231

[56] References Cited

U.S. PATENT DOCUMENTS 5,756,734  5/1998  Rinehart et al. .................. 544/231

OTHER PUBLICATIONS

Overman et al. "Enantioselective Total Synthesis of (–)Ptilomycalin" J. Am. Chem Soc. (1995), 117, 2657–2658.

Primary Examiner—Richard L. Raymond
Attorney, Agent, or Firm—Ernest V. Linek; Banner & Witcoff, Ltd.

[57] ABSTRACT

The present invention is directed to the isolation and characterization of six new crambescidin compounds, the structures of which are shown below:

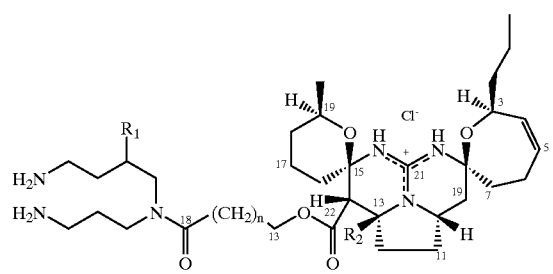

7 $R_1 = Cl, R_2 = OH, n = 14$
8 $R_1 = Cl, R_1 = H, n = 14$

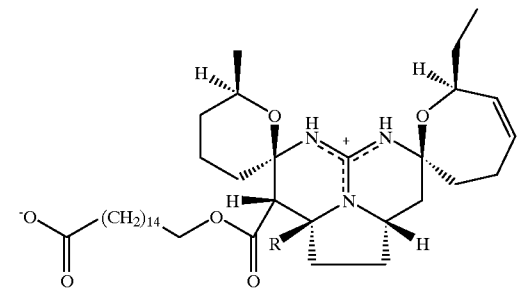

9 R = OH
10 R = H

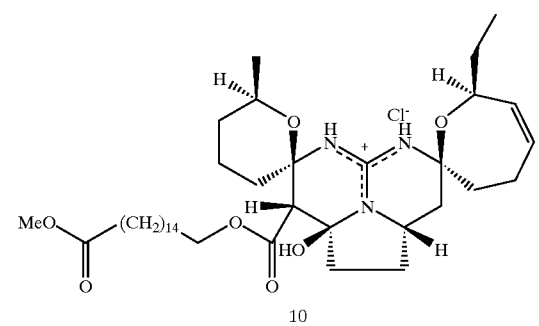

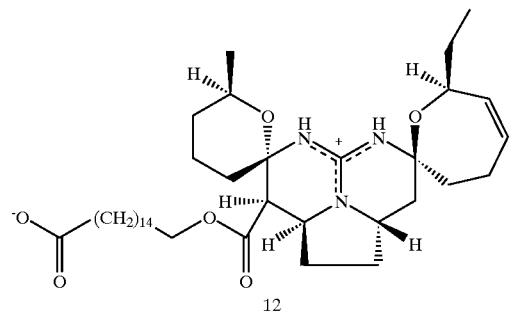

21 Claims, No Drawings

CRAMBESCIDIN COMPOUNDS

CROSS-REFERENCE TO RELATED APPLICATION

This application claims the benefit of U.S. Provisional Application Ser. No. 60/043,327 filed Apr. 15, 1997, the teachings of which are incorporated herein by reference.

BACKGROUND OF THE INVENTION

In the course of screening for novel bioactive agents from marine sponges, a new group of potent cytotoxic and antiviral compounds, crambescidins (1–5)[1–4] from the sponge *Crambe crambe* and ptilomycalin A (6) from the sponge *Ptilocaulis spiculifer* and a Hemimycale sp.,[5–7] possessing complex pentacyclic guanidines linked by a linear ω-hydroxy fatty acid to a hydroxyspermidine or spermidine unit, have been described. Extensive NMR studies have shown that the relative stereochemistry of the pentacyclic guanidine moieties of crambescidins (1–4) and ptilomycalin A (6) is identical, while oxidative degradation of crambescidin 816 (1)[2] and enantioselective total synthesis of ptilomycalin A (6)[8] have rigorously established their identical absolute configuration of the central guanidine moieties.

Recently the cooccurrence of crambescidins and ptilomycalin A was found in the sponge Batzella sp.[9]. Substantial cytotoxic, antiviral and antifungal activities have been described for crambescidins-[1–4] and ptilomycalin A[5–7], and crambescidin 816 has shown to be potent calcium channel blocker.[4]

In order to obtain substantial quantities of crambescidin 816 (1) for pre-clinical and clinical trials, three *Crambe crambe* samples were subjected to an isolation procedure similar to that described previously (see Experimental Section).[1–2] Total 1.48 g crambescidin 816 (1) together with the known crambescidins (2–5), ptilomycalin A (6) and six newly discovered crambescidin compounds (7–12) were isolated by FABMS guided isolation.

SUMMARY OF THE INVENTION

The structures and bioactivities of the new crambescidins (7–12) are the subject of the present invention. The chlorinated spermidine unit of crambescidins 834 (7) and 818 (8) is unprecedented from a natural source. The structures of the crambescidins are as follows:

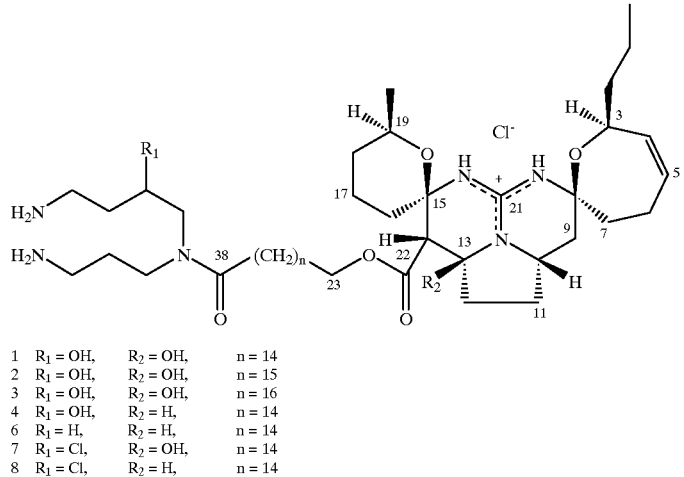

1  $R_1$ = OH, $R_2$ = OH, n = 14
2  $R_1$ = OH, $R_2$ = OH, n = 15
3  $R_1$ = OH, $R_2$ = OH, n = 16
4  $R_1$ = OH, $R_2$ = H,  n = 14
6  $R_1$ = H,  $R_2$ = H,  n = 14
7  $R_1$ = Cl, $R_2$ = OH, n = 14
8  $R_1$ = Cl, $R_2$ = H,  n = 14

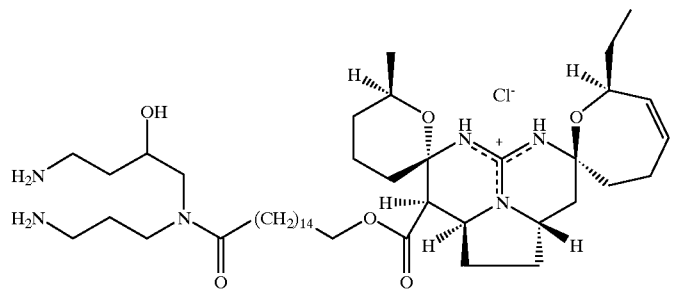

5

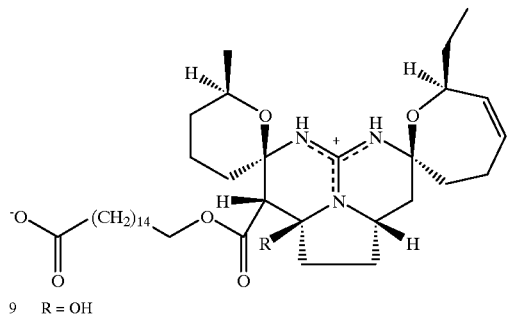

9  R = OH
11 R = H

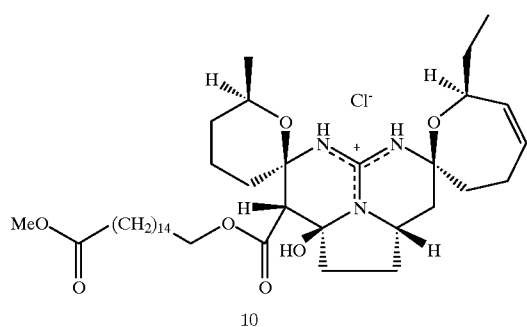

10

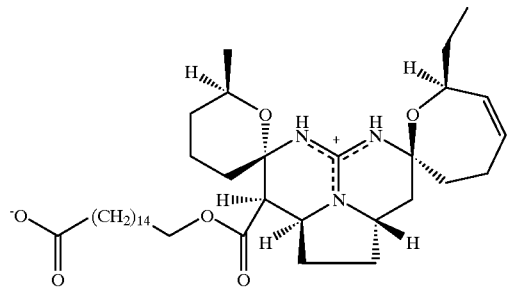

12

Structures of New Crambescidins (7–12).

Crambescidin 834 (7) was assigned the molecular formula $C_{45}H_{79}N_6O_6Cl$ by high-resolution fast atom bombardment mass spectrometry (HRFABMS) data [m/z 835.5821 (M+H, Δ 0.7 mmu)]. The presence of a chlorine and a free hydroxyl group were evident, since fragment ions for losses of hydrochloride (M+H–HCL, 799.6075, Δ −1.4 mmu) and water (M+H–HCL–H$_2$O, 781.5984, Δ −2.9 mmu) were observed in FABMS and FABMS/collision-induced dissociation (CID)/MS spectra of 7.

The structure of the hydroxyl pentacyclic guanidine moiety of 7 was assigned to be the same as that of 1 based on FABMS and NMR data. The fragment ions at m/z 420, 374, 358, 264 and 246, which are characteristic of the hydroxyl pentacyclic guanidine moiety in crambescidins (1–4),[1] were observed in FABMS and FABMS/CID/MS spectra of 7. The position of the hydroxyl group in the pentacyclic guanidine unit was assigned by COSY, HMQC, and HMBC NMR experiments, were nearly identical to those in crambescidins (1–4), suggesting that the position of the hydroxyl group and the stereochemistry of the hydroxyl pentacyclic guanidine moiety is the same in all these crambescidins.

The fragment ions of the side chain from C-23 to -45 were observed as intense peaks at m/z 398.3729 ($C_{23}H_{48}N_3O_2$, Δ 1.8 mmu) and 380.3636 ($C_{23}H_{46}N_3O$ Δ 0.5 mmu) in FABMS and FABMS/CID/MS of 7, they are absent in the spectra of other chlorinated crambescidins. A polymethylene chain from C-23 to -37 was indicated by NMR and especially, by FABMS/CID/MS data, which provided a nearly unbroken series of fragment ions from cleavage at successive methylene groups, from m/z 380 to 198.1616 ($C_{10}H_{48}N_3O$, Δ −1.0 mmu). The ester linkage between the side chain and the hydroxyl pentacyclic guanidine unit, suggested by the fragment ion at m/z 614.4549 ($C_{36}H_{60}N_3O_5$, Δ −1.6 mmu), was confirmed by the long range correlations between the carboxyl carbon at δ 168.12 (C-22) and protons at δ 3.48 (s, H-14) and 4.16 (t, H$_2$-23) in the HMBC spectrum of 7. Two isolated spin systems (from H-39b to H$_2$-41 and from H-42a, -42b to H$_2$-45) and the position of the chlorine in the chlorinated spermidine unit were identified from COSY and HMQC data. The two spin systems were connected each other by long-range C—H correlations, between C-42 (δ57.83) and H-39b (δ3.62) and between C-39 (δ47.19) and H-42a, -42b (δ3.36, 3.62) observed in the HMBC spectrum. Moreover, the amide linkage in 7 was established by the observation of the correlations between the second carboxyl carbon at δ 165.49 (C-38) and protons at δ 3.36 (H-42a), 2.49 (H-37a) and 2.76 (H-37b) in the HMBC spectrum.

Crambescidin 818 (8), assigned the molecular formula $C_{45}H_{79}N_6O_5Cl$ by HRFABMS (M+H, 819.5889, Δ −1.0 mmu), has one oxygen (hydroxyl group) less than crambescidin 834 (7). FABMS and FABMS/CID/MS spectra of 8 shown the fragment ion at m/z 783.6145 (Δ −3.3 mmu) corresponding to M+H−HCL, identifying the presence of a chlorine. At the same time, the presence of m/z 404 and 358 and the absence of m/z 420, 374, 264 and 246 indicated that crambescidin 818 (8) has the same pentacyclic guanidine portion as that of crambescidin 800 (4), which was confirmed by comparison of $^1$H and $^{13}$C data of 8 with those of 4.[1] $^1$H and $^{13}$C NMR chemical shifts of the chlorinated spermidine unit assigned by COSY data in 8 were nearly identical to those in 7 suggesting that the position and the stereochemistry of the chlorine in crambescidins 818 and 834 are the same.

Crambescidin 673 (9) was assigned the molecular formula $C_{38}H_{63}N_3O_7$ by HRFABMS data (M+H, 674.4734, Δ 1.0 mmu). FABMS and FABMS/CID/MS spectra of 9 shown the characteristic peaks for the hydroxyl pentacyclic guanidine unit in crambescidins at m/z 420, 358, 264, and 246 and a nearly unbroken series of homologous fragment ions from cleavage at successive methylene groups from m/z 628 to 420, suggesting that crambescidin 673 (9) has a carboxylic acid terminal, lacking a spermidine unit. This proposed structure was completely supported by the $^1$H and $^{13}$C NMR data for 10 and 9 indicated that crambescidin 687 (10) is the methyl ester of crambescidin 673 (9). The methoxyl group was observed at $\delta_H$ 3.65 and $\delta_C$ 51.44 in the NMR spectra for 10. The C-38 signal (δ174.39) in 10 was shifted upfield compared to the corresponding signal (δ181.60) in 9.

Crambescidin 687 (10) (HRFABMS, 688.4907, M+H; Δ −0.6 mmu for $C_{38}H_{66}N_3O_7$ by HRFABMS data (M+H, 674.4734, Δ 1.0 mmu). FABMS and FABMS/CID/MS spectra of 9 shown the characteristic peaks for the hydroxyl pentacyclic guanidine unit in crambescidins at m/z 420, 358, 264, and 246 and a nearly unbroken series of homologous fragment ions from cleavage at successive methylene groups from m/z 628 to 420, suggesting that crambescidin 673 (9) has a carboxylic acid terminal, lacking a spermidine unit. This proposed structure was completely supported by the $^1$H and $^{13}$C NMR data (see Tables 1 and 2) that were assigned with the aid of the COSY data. The carboxylic carbonyl signal was observed at δ 181.60.

Crambescidin 687 (10) (HRFABMS, 688.4907, M+H; Δ −0.6 mmu for $C_{39}H_{66}N_3O_7$), differing from 9 by a $CH_2$ group, shown similar FABMS and FABMS/CID/MS fragment ions to those of 9. Comparison of $^1$H and $^{13}$C NMR data for 10 and 9 indicated that crambescidin 687 (10) is the methyl ester of crambescidin 687 (10) is the methyl ester of crambescidin 673 (9). The methoxyl group was observed at $\delta_H$ 3.65 and $\delta_C$ 51.44 in the NMR spectra for 10. The C-38 signal (δ 174.39) in 10 was shifted upfield compared to the corresponding signal (δ 181.60) in 9.

Crambescidin 657 (11), assigned the molecular formula $C_{38}H_{66}N_3O_7$), differing from 9 by a $CH_{38}H63N_3O_6$ by HRFABMS (M+H, 658.4797, Δ −0.2 mmu), differing from 9 by an oxygen (hydroxy group). FABMS and FABMS/CID/MS spectra for 11 shown fragment ions at m/z 404 and 358, and a nearly unbroken series of fragment ions from cleavage at successive methylene groups from m/z 612 to 404, indicating the absence of an oxygen at C-13 in the pentacyclic guanidine portion, as confirmed by $^1$H and $^{13}$C NMR data in Tables 1 and 2.

13,14,15-Isocrambescidin 657 (12) was assigned the identical molecular formula $C_{38}H_{63}N_3O_6$ to that of 11 by HRFABMS data (n/z 658.4790, M+H, Δ 0.5 mmu). FABMS and FABMS/CID/MS spectral data for 12 were also identical to those for 11. However, chromatographic properties and the NMR patterns for 11 and 12 were similar but clearly distinguishable, indicating that they are isomers of each other. $^1$H and $^{13}$C NMR chemical shifts and coupling constants in the pentacylic guanidine unit in 12, assigned by COSY and TOCSY experiments, were very similar to those in 5,[2] suggesting that the stereochemistry for the pentacyclic guanidines moiety of 12 was further proven by the NOESY experiment, in which NOE's between H-10 and CH$_3$-1 and between H-14 and H-13, H-19 were observed, meanwhile the NOE between H-10 and H-13 was absent.[1,2]

Crambescidin 9, 11 or 12 has an acidic carboxylic acid terminal and a strongly basic pentacyclic guanidine portion,[6] thus they occur as the inner salt form. Two downfield exchangeable protons, correlated with H-9b and H-14 respectively by the COSY experiment, were observed in the $^1$H NMR spectrum (in CDCl$_3$) of 7, 8 or 10, indicating that the pentacyclic guanidine portion of these crambescidins is in the salt form. The nature of the counterion is not determined but, this is presumably Cl$^{-1}$ because several isolation steps involved contact with NaCl.

DETAILED DESCRIPTION OF THE INVENTION

As described above, the present invention is directed to the isolation and characterization (i.e., structures and bioactivities) of six new crambescidins (Compounds 7–12). These were determined as follows:

General. NMR spectra were obtained with U-500 or UI-500 (500-MHz, $^1$H; 125-MHz, $^{13}$C) spectrometers; chemical shifts (δ) are reported in ppm referenced to the solvent peaks. High- and low-resolution fast atom bombardment (FAB) mass spectra were measured on a ZAB-SE spectrometer, and FABMS/CID/MS spectra on a 70 SE-4F instrument using dithiothreitol-dithioerythritol as matrix.[10] A C-18 column (25×0.8 cm, 5-μm particle size) and CH$_3$OH:0.1 M NaCl (8:2) solvent were used for HPLC separation.

Extraction and Isolation. Isolation was guided by FABMS measurement on all extracts and separated fractions. Three *Crambe crambe* samples were involved.

The first sample was collected by SCUBA at Murcia, Spain, and was identified by Dr. M. J. Uriz-Lespe (Centred' Estudis Avancats de Blanes, Blanes, Spain). The frozen sample (100.2 g) was extracted with CHCl$_3$:toluene (3:1). The extract was evaporated in vacuo to give a residue (6.5 g), which was partitioned between CHCl$_3$ and 1.0 M NaCl (1:1, 50 mL×3). The organic layer (3.2 g) was further partitioned between the lower phase was purified by HPLC to give 1 (12.0 mg), 2 (7.0 mg), 3 (2.4 mg), 4 (0.4 mg) and 5 (5.4 mg).

The second frozen sample (500.0 g), collected at Ibiza, Spain, was isolated by following the same procedure to give crambescidin 816 (1, 104.5 mg).

The third sample (3208.0 g), was collected at Isla de Formentor (Cueva) Palma de Mallorca, Spain. The frozen sample was extracted with CHCl$_3$:toluene (3:1) to obtain an extract (143.0 g), which was partitioned between CHCl$_3$ and 1.0 M NaCl (1:1, 1000 mL×3). The CHCl$_3$ layer (55.4 g) was further partitioned with hexane:EtOAc:MeOH:H$_2$O (4:7:4:3). The lower phase (18.2 g), shown main peaks at m/z 817, 801 was chromatographed on a flash C-18 (200 g) column. The column was eluted with the lower layer of the mixed solvent [hexane:EtOAc:MeOH:H$_2$O (4:7:4:3)] to give two fractions, which were purified by HPLC to yield crambescidins 816 (1, 1367.4 mg), 843 (7, 4.4 mg), 818 (8, 3.1 mg) and ptilomycalin A (6, 2.9 mg). The upper phase (37.2 g), shown small peaks at m/z 658 and 674, was separated by flash chromatography on a silica gel (300 g, 230–400 mesh) column, eluting with a solvent gradient system increasing methanol (0%–100%) in CHCl₃ (100%–0%). The fractions shown peaks at m/z 658, 674, and 688 were further purified by repeated silica gel (230–400 mesh) column chromatography using CHCl₃:EtOAc:MeOH (9:9:1), CHCL₃:MeOH (15:1) and CHCl₃:MeOH (9:1) as solvent systems to yield crambescidins 673 (9, 23.8 mg), 687 (10, 14.7 mg), 657 (11, 3.4 mg) and 13, 14, 15-isocrambescidin 657 (12, 6.6 mg).

Crambeacidin 834 (7): colorless gum $[\alpha]^{25}D$ -24.7° (c 0.44, MeOH); FABMS m/z 835 (M+H), 799 (M+H–HCl, $C_{45}H_{79}N_6O_6$, HRFABMS 799.6075, Δ-1.4 mmu), 781 (M+H–HCl–H₂O, $C_{45}H_{79}N_6O_6$, HRFABMS 799.6075, Δ-2.9 mmu), 694, 655, 614 ($C_{36}H_{60}N_3O_5$, HRFABMS 781.5984, Δ-2.9 mmu), 694, 655, 614 ($C_{36}H_{60}N_3O_5$, HRFABMS 614.4549, Δ-1.6 mmu), 426, 420, 398 ($C_{23}H_{48}N_3O_2$, HRFABMS 398.3729, Δ 1.8 mmu), 380 ($C_{23}H_{46}N_3O$, HRFABMS 380.3636, Δ 0.5 mmu), 374, 358, 314, 264, 246, 198 ($C_{10}H_{20}N_3O$, HRFABMS 198.1616, Δ-1.0 mmu); ¹H NMR (CD₃OD) see Table 1; ¹³C NMR (CD₃OD) see Table 1; ¹³C NMR (CD₃OD) see Table 2; ¹H NMR (CDCl₃) δ: 0.88 (t, J=7, H₃-1), 1.46 (m, H-2a), 1.54 (m, H-2b), 4.51 (br d, J=10, H-3), 5.49 (br d, J=11, H-4), 5.67 (brdd, J=11, 7.5, H-5), 2.19 (m, H-9a), 2.34 (m, H-6b), 1.94 (m, H-7a), 2.47 (br t, J=14, H-7b), 1.42 (t, J=12.5, H-9a), 2.56 (dd, J=12.5, 5, H-9b), 4.32 (m, H-10), 1.57 (m, H-11a), 2.33 (m, H-11b), 2.04 (ddd, J=14, 10, 4.5, H-12a), 2.16 (m, H-12b), 3.36 (s, H-14), 1.62 (m, H-16a), 1.77 (ddd, J=14, 14, 4.5, H-16b), 1.76 (m, H-17a), 2.32 (m, H-17b), 1.23 (m, H-18a), 1.76 (dddd, J=14, 7, 7, 2, H-18b), 4.09 (m, H-19), 1.10 (d, J=6, H-20), 4.09 (m, H₂-23), 1.61 (m, H₂-40), 3.43 (br, H₂-41), 3.27 (br, H₂-42), 3.79 (br, H-43), 1.68 (m, H-44a), 2.15 (m, H-44b), 2.75 (br, H-45a), 2.86 (br, H-45B), 5.83 (s, H-130H), 10.01 (br s, H-8N), 10.07 (br s, H-15N); ¹³C NMR (CDCl₃) δ:10.16 (C-1), 29.09 (c-2), 71.29 (C-3), 133.66 (C-4), 129.84 (C-5), 23.44 (C-6), 36.90 (C-7), 83.56 (C-8), 37.03 (C-9), 52.41 (C-10), 29.53 (C-11), 37.19 (C-12), 88.68 (C-13), 54.55 (C-14), 83.04 (C-15), 32.09 (C-16), 18.00 (C-17), 31.56 (C-18), 68.84 (C-19), 21.43 (C-20), 148.13 (C-21), 167.17 (C-22), 65.93 (C-23), 28.38 (C-24), 25.78 (C-36), 32.19 (C-37), 165.01 (C-38), 47.21 (C-39), 19.10 (C-40), 38.74 (C-41), 57.50 (C-42), 65.05 (C-43), 31.71 (C-44), 37.04 (C-45); HRFABMS calc Mr for $C_{45}H_{80}N_6O_6Cl$ 835.5828 (M+H)⁺, found Mr 835.5821.

Crambescidin 818 (8): colorless gum, $[\alpha]^{25}D$-11.4° (c 0.31, MeOH); FABMS m/z 819 (M+H), 783 (M+H–HCl, $C_{45}H_{79}N_6O_5$, HRFABMS 783.6145, Δ -3.3 mmu), 696 ($C_{41}H_{70}N_5O_4$, HRFABMS 696.5437, Δ -0.09 mmu), 639, 612, 598, 404, 430, 398, 380, 358, 288, 260, 206; ¹H NMR (CD₃OD) see Table 1; ¹³C NMR (CD₃OD) see Table 2; ¹H NMR (CDCl₃) δ:0.83 (t, J=7, H-1), 1.42 (m, H-2a), 1.53 (m, H-2b), 4.50 (br d, J=9.5, H-3). 5.48 (br d, J=11, H-4), 5.68 (br dd, J=11, 7, H-5), 2.18 (m, H-6a), 2.34 (m, H-6b), 1.69 (m, H-7a), 2.46 (br t, J=13, H-7b), 1.41 (t, J=12.5, -9a), 2.55 (dd, J=12.5, 4.5, H-9b), 3.96 (m, H-10), 1.61 (m, H-11a), 2.21 (m, H-11b), 1.79 (m, H-12a), 2.27 (m, H-12b), 4.28 (ddd, 10, 5, 5, H-13), 2.94 (d, J=5, H-14), 1.79 (m, H₂-16), 1.79 (m, H₂-17), 1.20 (m, H-18a), 1.71 (m, H-18b), 3.96 (m, H-19), 1.05 (d, J=6, H-20), 4.09 (m, H₂-23), 1.61 (m, H₂-24), 1.60 (m, H₂-36) 2.02 (m, H₂-37), 3.48 (br, H₂-40), 3.43 (br, H₂-41), 3.28 (br, H₂-42), 3.80 (br, H-43), 1.75 (m, H-44b), 2.77 (br, H-45a), 2.85 (br, H-45b), 9.53 (br s, H-8n), 9.77 (br s, H-15N); ¹³C NMR (CDCl₃) δ: 10.09 (C-1), 29.11 (C-2), 71.03 (C-3), 133.69 (C-4), 129.94 (C-5), 23.42 (C-6), 36.97 (C-7), 83.59 (C-8), 36.99 (C-9), 53.95 (C-10), 30.66 (C-11), 26.84 (C-12), 51.84 (C-13), 49.67 (C-14), 80.71 (C-15), 31.92 (C-16), 18.40 (C-17), 31.96 (C-18), 67.29 (C-19), 21.46 (C-20), 148.85 (C-21), 168.39 (C-22), 65.46 (C-23), 28.47 (C-24), 25.79 (C-36), 31.92 (C-37), 165.04 (C-38); HRFABMS calcd Mr for $C_{45}H_{80}N_6O_5$ Cl 819.5879 (M+H)⁺, found Mr 819.5889.

Crambescidin 673 (9): colorless gum $[\alpha]^{25}D$-16.6 (c0.50, MeOH); FABMS m/z 674 (M+H), 576, 420, 358, 314 ($C_{19}H_{28}N_3O$, HRFABMS 314.2240, Δ -0.8 mmu), 264, 246, 168; ¹H NMR see Table 1; ¹³C NMR see Table 2; HRFABMS calcd Mr for $C_{38}H_{64}N3O_7$ 674.4744 (M+H)⁺, found Mr 674.4734.

Crambescidin 687 (10): colorless gum, $[\alpha]^{25}D$ -18.2° (c0.52, MeOH); FABMS m/z 688 (M+H), 630, 590, 420, 374, 358, 314, 264, 246, 168; ¹H NMR see Table 1; ¹³C NMR see Table 2; HRFABMS calcd Mr for $C_{39}H_{66}N_3O_7$ 688.4901 (M+H)⁺, found Mr 688.4907.

Crambescidin 657 (11): colorless gum, $[\alpha]^{25}D$- -12.1° (c0.34, MeOH); FABMS m/z 658 (M+H), 612, 560, 404 ($C_{22}H_{34}N_3O_4$, HRFABMS 404.2541, Δ 0.8 mmu), 360, 358, 288, 206, ($C_{13}H_{20}NO$, HRFABMS 206.1547, Δ -0.2 mmu); ¹H NMR see Table 1; ¹³C NMR see Table 2; HRFABMS calcd Mr for $C_{38}H_{64}N_3O_6$ 658.4795 (M+H)⁺, found Mr 658.4797.

Methanation of Crambescidin 657:

A mixture of 11 (1 mg) dissolved in MeOH (1 mL) and diazomethane in Et2O (2 mL) was kept at room temperature for 24 h. The solvents were removed (N₂) and the residue was chromatographed on silica gel using CHCl₃:MeOH (9:1) as a solvent system to yield the methyl ester of 11 (0.7 mg). Colorless gum, FABMS m/z 672 (M+H), 574, 404, 358, 288, 206; HRFABMS calcd Mr for $C_{39}H_{66}N_3O_6$ 672.4952 (M+H)⁺, found Mr 672.4984.

13,14,15-Isocrambescidin 657 (12): colorless gum, $[\alpha]^{25}D$ -32.7° (c 0.29, MeOH); FABMS m/z 658 (M+H), 612, 560 ($C_{32}H_{54}N_3O_5$, HRFABMS 560.4034, Δ 2.9 mmu), 404, 360, 358 ($C_{21}H_{32}N_3O_2$, HRFABMS 358.2494, Δ 0.1 mmu), 288, 206; ¹H NMR see Table 1; ¹³C NMR see Table 2; HRFABMS calcd Mr $C_{38}H_{64}N_3O_6$ 658.4795 (M+H)⁺, found Mr 658.4790.

Table 1 provides ¹H NMR data for compounds 7–12. Table 2 provides ¹³C NMR data for compounds 7–12.

TABLE 1

¹H NMR Data for Compounds 7–12

| H No. | 7 (CD₃OD) | 8 (CD₃OD) | 9 (CDCl₃) | 10 (CDCl₃) | 11 (CDCl₃) | 12 (CDCl₃) |
|---|---|---|---|---|---|---|
| 1 | 0.89, t, 7 | 0.85, t, 7 | 0.86, t, 7 | 0.87, t, 7 | 0.82, t, 7 | 0.94, t, 7.5 |
| 2a | 1.49, m | 1.48, m | 1.45, m | 1.46, m | 1.42, m | 1.47, m |
| 2b | 1.57, m | 1.55, m | 1.54, m | 1.55, m | 1, 53, m | 1.51, m |
| 3 | 4.46, br d, 10 | 4.42, br d, 9.5 | 4.52, br d, 10 | 4.51, br d, 10 | 4.38, br d 9.5 | 4.63, br s |

TABLE 1-continued

¹H NMR Data for Compounds 7–12

| H No. | 7 (CD₃OD) | 8 (CD₃OD) | 9 (CDCl₃) | 10 (CDCl₃) | 11 (CDCl₃) | 12 (CDCl₃) |
|---|---|---|---|---|---|---|
| 4 | 5.52, br d, 11 | 5.51, br d, 11 | 5.48, br d, 11 | 5.48, br d, 11 | 5.48, br d, 11 | 5.50, br d, 11 |
| 5 | 5.72, br dd, 11, 7 | 5.72, br dd, 11, 7 | 5.64, br dd, 11, 7 | 5.66, br dd, 11, 7 | 5.64, br dd, 11, 7 | 5.62, br dd, 11, 7 |
| 6a | 2.18, m | 2.18, m | 2.12, m | 2.18, m | 2.14, m | 2.10, m |
| 6b | 2.44, m | 2.42, m | 2.33, m | 2.34, m | 2.32, m | 2.30, m |
| 7a | 2.02, m | 2.02, m | 1.81, m | 1.92, m | 1.84, m | 1.78, m |
| 7b | 2.37, br t, 13.5 | 2.33, br t, 13.5 | 2.73 br t, 14 | 2.51, br t, 14.5 | 2.74, br t, 14 | 2.73, br t, 13.5 |
| 9a | 1.44, t, 12.5 | 1.44, t, 13 | 1.32, t, 12.5 | 1.41, t, 12.5 | 1.31, t, 12.5 | 1.35, t, 12.5 |
| 10 | 4.32, m | 4.05, m | 4, 32, m | 43.2, m | 3.98, m | 3.89, m |
| 11a | 1.61, m | 1.60, m | 1.55, m | 1.57, m | 1.61, m | 1.55, m |
| 11b | 2.43, m | 2.29, m | 2.30, m | 2.33, m | 2.14, m | 2.19, m |
| 12a | 2.06, m | 1.86, m | 1.98, m | 2.03, m | 1.78, m | 1.62, m |
| 12b | 2.18, m | 2.31, m | 2.14, m | 2.16, m | 2.24, m | 2.15, m |
| 13 | | 4.35, m | | | 4.26, m | 3.98, m |
| 14 | 3.48, s | 3.08, d, 5 | 3.31, 3 | 3.35, s | 2.89, d, 4 | 3.48, d, 3.5 |
| 16a | 1.65, m | 1.68, m | 1.68, m | 1.62, m | 1.62, m | 1.62, m |
| 16b | 1, 87, m | 1.76, m | 1.74, m | 1.76, m | 2.02, m | 1.71, m |
| 17a | 1.84, m | 1.75, m | 1.67, m | 1.76, m | 1.67, m | 1.69, m |
| 17b | 1.96, m | 1.82, m | 2.44, m | 2.32, m | 2.44, m | 2.01, m |
| 18a | 1.33, m | 1.26, m | 1.21, m | 1.23, m | 1.21, m | 1.29, m |
| 18b | 1.73, m | 1.72, m | 1.66, m | 1.76, m | 1.67, m | 1.59, m |
| 19 | 3.97, m | 3.84, m | 4.00, m | 4.08, m | 3.99, m | 3.69, m |
| 20 | 1.14 d, 6 | 1.04, d, 6 | 1.05, d,6 | 1.08, d, 6.5 | 1.04, d, 6.5 | 1.17, d, 6 |
| 23a | 4.16, t, 6.5 | 4.13, dt, 6.5, 2 | 4.01, m | 3.96, m | 3.96, m | 3.97, m |
| 24 | 1.66, m | 1.65, m | 1.60, m | 1.60, m | 1.60, m | 1.57, m |
| 36 | 1.64, m | 1.65, m | 1.56, m | 1.60, m | 1.60, m | 1.54, m |
| 37a | 2.49, m | 2.50, m | 2.22, t, 7 | 2.23, t, 7 | 2.23, t, 7 | 2.23, t, 7 |
| 37b | 2.76, m | 2, 76, m | 2.22. t, 7 | 2,23, t, 7 | 2.23, t, 7 | 2.23, t, 7 |
| 39a | 3.53, dt, 13, 5 | 3.45, dt, 14, 5 | | | | |
| 39b | 3.62, dt, 13.5 | 3.61, dt, 14, 5 | | | | |
| 40 | 2.05, m | 2.05, m | | | | |
| 41 | 3.40, t, 5 | 3.40, t, 5 | | | | |
| 42a | 3.36, dd, 15, 3 | 3.36, dd, 15, 3 | | | | |
| 42b | 3.62, dd, 15, 10 | 3.61, dd, 15, 10 | | | | |
| 43 | 4.06, m | 4.05, m | | | | |
| 44a | 1.74, m | 1.73, m | | | | |
| 44b | 1.85, m | 1.84, m | | | | |
| 45 | 3.13, m | 3.13, m | | | | |
| 13 OH | 5.86, s | 5.84, s | | | | |
| OMe | | | | 3.65, s | | |

TABLE 2

¹³C NMR Data for Compounds 7–12

| C No. | 7 (CD₃OD) | 8 (CD₃OD) | 9 (CDCl₃) | 10 (CDCl₃) | 11 (CDCl₃) | 12 (CDCl₃) |
|---|---|---|---|---|---|---|
| 1 | 10.26 | 10.12 | 10.22 | 10.14 | 10.17 | 10.30 |
| 2 | 29.70 | 29.57 | 29.06 | 29.10 | 29.18 | 29.14 |
| 3 | 71.83 | 71.64 | 70.70 | 71.26 | 70.57 | 70.36 |
| 4 | 133.54 | 133.62 | 133.84 | 133.67 | 133.91 | 133.89 |
| 5 | 130.59 | 130.66 | 129.78 | 129.75 | 129.88 | 129.62 |
| 6 | 23.73 | 23.74 | 23.72 | 23.45 | 23.77 | 24.37 |
| 7 | 36.88 | 37.19 | 36.78 | 36.88 | 36.83 | 37.41 |
| 8 | 84.44 | 84.41 | 83.53 | 83.60 | 83.66 | 85.00 |
| 9 | 38.98 | 37.67 | 37.77 | 37.11 | 37.78 | 37.34 |
| 10 | 53.41 | 54.90 | 52.21 | 52.40 | 53.80 | 52.88 |
| 11 | 30.00 | 30.78 | 29.66* | 29.67 | 30.66* | 30.26 |
| 12 | 37.52 | 26.88 | 35.70 | 36.88 | 26.85 | 29.64* |
| 13 | 89.86 | 53.47 | 88.44 | 88.69 | 51.58 | 51.99 |
| 14 | 55.17 | 49.97 | 55.59 | 54.64 | 50.64 | 41.48 |
| 15 | 83.82 | 81.48 | 83.15 | 83.08 | 80.64 | 83.20 |
| 16 | 31.90 | 31.91 | 29.45* | 32.08 | 31.91* | 29.68* |
| 17 | 18.46 | 18.77 | 17.60 | 17.94 | 17.95 | 19.90 |
| 18 | 31.76 | 32.27* | 31.67* | 31.53 | 32.19** | 31.58** |
| 19 | 69.34 | 67.75 | 68.09 | 68.82 | 66.71 | 68.81 |
| 20 | 21.00 | 21.09 | 21.49 | 21.41 | 21.59 | 22.25 |
| 21 | 148.86 | 149.54 | 148.85 | 148.12 | 149.48 | 149.74 |
| 22 | 168.12 | 169.54 | 167.37 | 167.16 | 168.59 | 168.17 |
| 23 | 66.38 | 65.85 | 65.57 | 65.91 | 65.07 | 65.06 |
| 24 | 28.83 | 28.95 | 28.24 | 28.39 | 28.66 | 28.30 |
| 36 | 26.98 | 26.33 | 25.65 | 25.79 | 25.61 | 25.53 |
| 37 | 32.08 | 32.38* | 32.18** | 34.10 | 32.09** | 31.91** |
| 38 | 165.49 | 165.56 | 181.60 | 174.39 | 181.38 | 180.53 |
| 39 | 47.19 | 47.19 | | | | |
| 40 | 19.15 | 19.14 | | | | |
| 41 | 39.26 | 39.26 | | | | |
| 42 | 57.83 | 57.83 | | | | |
| 43 | 66.38 | 66.42 | | | | |
| 44 | 32.02 | 32.08 | | | | |
| 45 | 37.69 | 37.69 | | | | |
| OMe | | | | 51.44 | | |

Signals marked * or ** may be interchanged.

Biological Activity. Crambescidins (1–4) inhibited the growth of L1210 cells,[1] crambescidin 816 (1) also exhibited antiviral activity against Herpes simple-x, Type I virus (HSV-I) and was shown to be a strong $Ca^{2+}$ channel blocker.[4] 13, 14, 15-Isocrambescidin 800 (5) was substantially less cytotoxic to L1210 cells, and had no observed antiviral activity.[2] Ptilomycalin A (6) shown cytotoxicity against L1210, P388, and KB cells, antifungal activity against *Candida albicans,* as well as antiviral activity (HSV).[5,6]

In a parallel assay against L1210 murine leukemia cells (see Table 3), using crambescidin 816 (1) as a standard, crambescidins 834 (7) and 818 (8) with a chlorinated spermidine unit are about 5 times more active than 1. However, crambescidins 674 (9) and 687 (10) without a spermidine derivative unit are less than 5 times as active than 1. 13, 14, 15-Isocrambescidin 657 (12) as expected in substantially less active (no inhibition at 5 $\mu$g/mL) than other crambescidins. Ptilomycalin A (6) is slightly more active than 1.

Meanwhile, in a antimicrobial assay against *Rhodotorula glutinis* crambescidins with a spermidine derivative derivative unit and ptilomycalin A shown to be active at 2 $\mu$g/well, other crambescidins did not show any activity at 20 $\mu$g/well. These observations revealed that both the cage-like structure of the pentacyclic moieties and the spermidine or its derivative unit in the crambescidins and ptilomycalin A play important roles in their strong biological activities.

Interestingly, crambescidin 657 (11) shows to be the most cytotoxic compound in the test. See especially Table 4. The activity is significantly decreased by the methanation with diazomethane. Because the acidic terminal of the side chain is folded toward the basic pentacyclic guanidine portion in the inner salt form of 11, and the conformation of the inner salt is different from thof other crambescidins, the cytotoxicity of 11 might come from a different action mechanism to the cells.

The new crambescidin compounds will have pharmaceutical uses comparable to the previously known crambescidin compounds, particularly as antiumor compounds, as shown in Tables 3 and 4.

compositions containing the active compounds identified herein and methods of treatment employing such pharmaceutical compositions.

The antitumor activities of the compounds have been determined in vitro in cell cultures of mouse leukemia P-388, human lung carcinoma A-549, human colon carcinoma HT-29 and human melanoma MEL-28. The procedure was carried out using the methodology described by Bergeron, et al., *Biochem. Biophys. Res. Comm.*, 121:848, 1984 and by Schroeder, et al.,*J. Med. Chem.*, 24:1078, 1981.

The active compounds of the present invention exhibit antitumor activity against mammalian tumors such as P-388 murine leukemia, A-549 human lung carcinoma, HT-29 human colon carcinoma, and MEL-28 human melanoma. The present invention thus includes a method of treating any mammal affected by a malignant tumor sensitive to these compounds, which comprises administering to the affected individual a therapeutically effective amount of an active compound or mixture of compounds, or pharmaceutical compositions thereof.

The present invention also relates to pharmaceutical compositions that contain as active ingredient one or more of the compounds of this invention, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

TABLE 3

Cytotoxicities against L1210 Cells for Compounds 1, 6–12, and Methyl 11

| Concentration ($\mu$g/mL) | Inhibition (%) | | | | | | | | |
|---|---|---|---|---|---|---|---|---|---|
| | 1 | 6 | 7 | 8 | 9 | 10 | 11 | 12 | Methyl 11 |
| 1.0 | 100 | 100 | 100 | 100 | 100 | 100 | 100 | 100 | 0 |
| 0.5 | 97 | 99 | 95 | 95 | 0 | 0 | 100 | 0 | 0 |
| 0.25 | 70 | 60 | 95 | 95 | 0 | 0 | 100 | 0 | 0 |
| 0.1 | 0 | 20 | 90 | 90 | 0 | 0 | 93 | 0 | 0 |

TABLE 4

Cytotoxicities against Tumor Cell Lines

| Crambescidins | P-388 | A-549 | $\mu$g/ml HT-29 | MEL-28 |
|---|---|---|---|---|
| 834 (7) | 0.05 | 0.05 | 0.05 | 0.05 |
| 818 (8) | 0.1 | 0.1 | 0.1 | 0.1 |
| 673 (9) | Nd | Nd | Nd | Nd |
| 687 (10) | Nd | Nd | Nd | Nd |
| 657 (11) | 0.25 | 0.05 | 0.05 | 0.05 |
| 816 (1) | 0.5 | 0.5 | 0.4 | |

Nd: Activity not determined.

The compounds of the present invention have been isolated (or semi-synthetically prepared) in substantially pure form, i.e., at a purity level sufficient to allow physical and biological characterization thereof. As described above, these compounds have been found to possess specific antitumor activities and as such they will be useful as medicinal agents in mammals, particularly in humans. Thus, another aspect of the present invention concerns pharmaceutical The correct dosage of a pharmaceutical composition comprising the compounds of this invention will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

REFERENCES

The following references provide background information related to this invention.
(1) Jares-Erijiman, E. A. Sakai, R; Rinehart, K. L. *J. Org. Chem.* 1991, 56, 5712–5715.
(2) Jares-EriJiman, E. A.; Ingrum, A. L.; Carney, J. R.; Rinehart, K. L.; Sakai, R. *J. Org. Chem.* 1993, 58, 4805–4808.
(3) Taveras, R.; Daloze, D.; Braekman, J. C.; Hajdue, E. *Biocherr Syst. Ecol.* 1994, 22, 645.
(4) Berlinck, R. G. S.; Braekman, J. C. Daloze, D.; Bruno, I.; Riccio, R.; Ferri, S.; Spampinato, S.; Speroni, E. *J. Nat. Prod.* 1993, 56, 1007–1015.

(5) Kashman, Y.; Hirsch, S.; McConnell, O. J.; Ohtani, I.; Kusumni, T.; Kakisawa, H. *J. Am. Chem. Soc.* 1989, 111, 8925–8926.
(6) Ohtani, I.; Kusumi, T.; Kakisawa, H.; Kashman, Y.; Hirsh, S. *J. Am. Chem. Soc.* 1992, 114, 8472–8479.
(7) Ohtani, I.; Kusumi, T.; Kakisawa, H. *Tetrahedron Lett.* 1992, 33, 2525–2528.
(8) Overman, L. E.; Rabinowitz, M. H.; Renhowe, P. A. *J. Am. Chem. Soc.* 1995, 117, 2657–2658.
(9) Patil, A. D.; Kumar, N. V.; Kokke, W. C.; Bean, M. F.; Freyer, A. J.; Brosse, C. D.; Mai, S.; Truneh, A.; Faulkner, D. J.; Carte, B.; Breen, A. L.; Hertzberg, R. P.; Johnson, R. K.; Westley, J. W.; Potts B. C. M. *J. Org. Chem.* 1995, 60, 1182–1188.
(10) Witten, J. L.; Schaffer, M. H.; O'Shea, M.: Cook, J. C.; Hemling, M. E.; Rinehart, K. L., Jr. *Biochem, Biophys. Res. Commun.* 1984, 124, 350–358.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The compound Crambescidin 834, isolated from the sponge *Crambe crambe,* having the following structure:

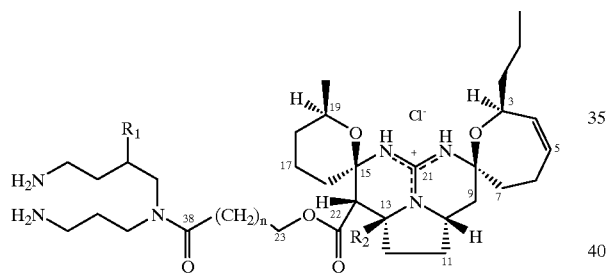

wherein $R_1$ is Cl, $R_2$ is OH and n=14, and pharmaceutically acceptable salts thereof.

2. The compound Crambescidin 818, isolated from the sponge *Crambe crambe,* having the following structure:

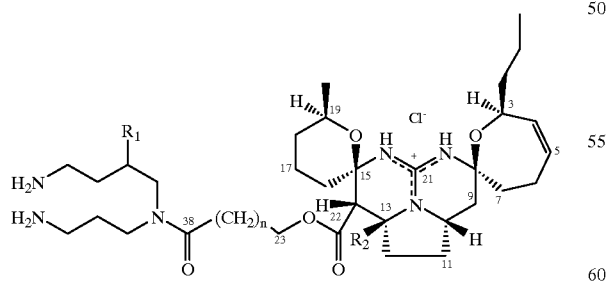

wherein $R^1$ is Cl, $R_2$ is H and n=14, and pharmaceutically acceptable salts thereof.

3. The compound Crambescidin 673, isolated from the sponge *Crambe crambe,* having the following structure:

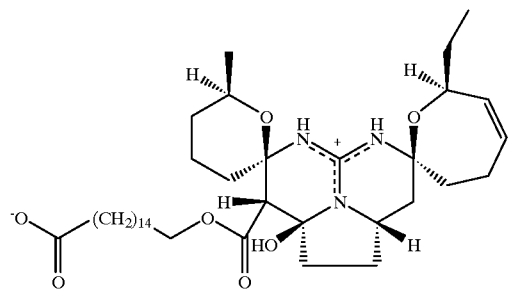

and pharmaceutically acceptable salts thereof.

4. The compound Crambescidin 687, isolated from the sponge *Crambe crambe,* having the following structure:

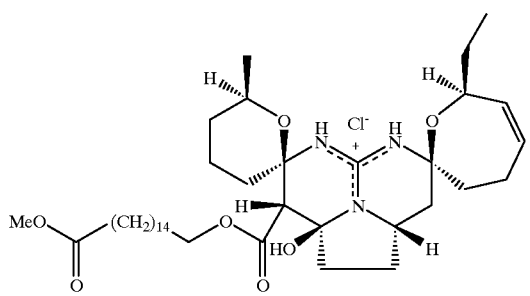

and pharmaceutically acceptable salts thereof.

5. The compound Crambescidin 657, isolated from the sponge *Crambe crambe,* having the following structure:

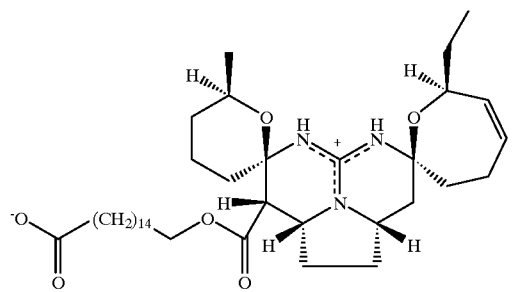

and pharmaceutically acceptable salts thereof.

6. The compound 13,14,15-Isocrambescidin 657, isolated from the sponge *Crambe crambe,* having the following structure:

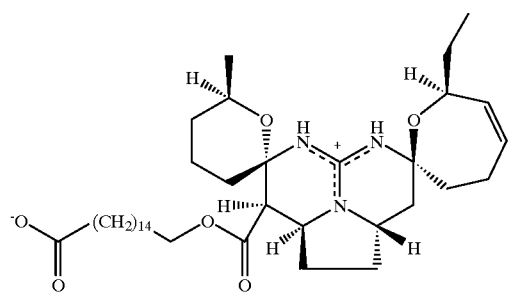

and pharmaceutically acceptable salts thereof.

7. The compound methyl Crambescidin 657, isolated from the sponge *Crambe crambe,* having the following structure:

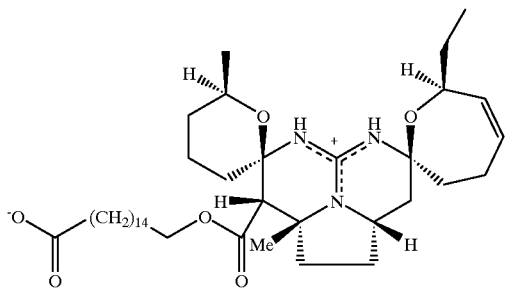

and pharmaceutically acceptable salts thereof.

8. A pharmaceutical or veterinary composition comprising Crambescidin 834 and a pharmaceutically acceptable carrier, diluent or excipient.

9. A pharmaceutical or veterinary composition comprising Crambescidin 818 and a pharmaceutically acceptable carrier, diluent or excipient.

10. A pharmaceutical or veterinary composition comprising Crambescidin 673 and a pharmaceutically acceptable carrier, diluent or excipient.

11. A pharmaceutical or veterinary composition comprising Crambescidin 687 and a pharmaceutically acceptable carrier, diluent or excipient.

12. A pharmaceutical or veterinary composition comprising Crambescidin 657 and a pharmaceutically acceptable carrier, diluent or excipient.

13. A pharmaceutical or veterinary composition comprising 13,14,15 Isocrambescidin 657 and a pharmaceutically acceptable carrier, diluent or excipient.

14. A pharmaceutical or veterinary composition comprising methyl Crambescidin 657 and a pharmaceutically acceptable carrier, diluent or excipient.

15. A method of treating a patient suffering from a mammalian tumor selected from the group consisting of leukemia, lung carcinoma, colon carcinoma and melanoma, comprising administering to said patient, an effective anti-tumor amount of Crambescidin 834 and a pharmaceutically acceptable carrier, diluent or excipient.

16. A method of treating a patient suffering from a mammalian tumor selected from the group consisting of leukemia, lung carcinoma, colon carcinoma and melanoma, comprising administering to said patient, an effective anti-tumor amount of Crambescidin 818 and a pharmaceutically acceptable carrier, diluent or excipient.

17. A method of treating a patient suffering from a mammalian tumor selected from the group consisting of leukemia, lung carcinoma, colon carcinoma and melanoma, comprising administering to said patient, an effective anti-tumor amount of Crambescidin 673 and a pharmaceutically acceptable carrier, diluent or excipient.

18. A method of treating a patient suffering from a mammalian tumor selected from the group consisting of leukemia, lung carcinoma, colon carcinoma and melanoma, comprising administering to said patient, an effective anti-tumor amount of Crambescidin 687 and a pharmaceutically acceptable carrier, diluent or excipient.

19. A method of treating a patient suffering from a mammalian tumor selected from the group consisting of leukemia, lung carcinoma, colon carcinoma and melanoma, comprising administering to said patient, an effective anti-tumor amount of Crambescidin 657 and a pharmaceutically acceptable carrier, diluent or excipient.

20. A method of treating a patient suffering from a mammalian tumor selected from the group consisting of leukemia, lung carcinoma, colon carcinoma and melanoma, comprising administering to said patient, an effective anti-tumor amount of 13,14,15 Isocrambescidin 657 and a pharmaceutically acceptable carrier, diluent or excipient.

21. A method of treating a patient suffering from a mammalian tumor selected from the group consisting of leukemia, lung carcinoma, colon carcinoma and melanoma, comprising administering to said patient, an effective anti-tumor amount of Methyl Crambescidin 657 and a pharmaceutically acceptable carrier, diluent or excipient.

* * * * *